United States Patent [19]

Anderson

[11] Plant 4,789

[45] Nov. 10, 1981

[54] NECTARINE TREE

[76] Inventor: Frederic W. Anderson, 826 W. 22nd St., Merced, Calif. 95340

[21] Appl. No.: 189,215

[22] Filed: Sep. 22, 1980

[51] Int. Cl.[3] ..... A01H 5/00

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A dwarf nectarine tree which is large for such type of tree, medium vigorous, spreading, open, vase-formed, and hardy; foliated with large, lanceolate, acutely pointed leaves having a crenate margin, medium length petiole, and alternate, reniform glands; blooms medium season from buds which are hardy and of medium size and length; the flowers being large and pink; and the tree being a regular and productive bearer of medium size, uniform, symmetrical, globose-oblong, early mid-season freestone fruit having yellow skin substantially overspread with red, and yellow flesh.

1 Drawing Figure

CLASSIFICATION OF THE VARIETY

The present variety of nectarine tree is embraced by Class 41, Plants, of the U.S. Patent Office Manual of Classification.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of dwarf nectarine tree was originated by me as an open pollinated seedling of an unnamed dwarf nectarine tree; the variety, as so originated, having been grown under careful and continuing observation, and—upon evidencing desirable characteristics for commercial production—the variety was selected for asexual reproduction.

ASEXUAL REPRODUCTION OF THE VARIETY

Subsequent to origination and selection by me of the present variety of dwarf nectarine tree, I asexually reproduced it by top-working on orchard trees, and—in maturity—such reproduction ran true to the original tree in all respects.

SUMMARY OF THE VARIETY

The present variety of dwarf nectarine tree is large for such type of tree, medium vigorous, spreading, open, vase-formed, and hardy; foliated with large, lanceolate, acutely pointed leaves having a crenate margin, medium length petiole, and alternate, reniform glands; blooms medium season from buds which are hardy and of medium size and length; the flowers being large and pink; and the tree being a regular and productive bearer of medium size, uniform, symmetrical, globose-oblong, early mid-season, freestone fruit having yellow skin substantially overspread with red, and yellow flesh.

The present variety of dwarf nectarine tree, while large for the type, is less than one-half the height of conventional or full-size nectarine trees, bears fruit quite heavily, and produces satisfactorily under a wide range of growing conditions.

BRIEF DESCRIPTION OF THE DRAWING

The drawing is an illustration, by photographic reproduction in color, of a twig with leaves, separate fruit, and a separate stone; one fruit being partially cut away to expose the flesh.

DESCRIPTION OF THE VARIETY

The botanical details of this new and distinct variety of dwarf nectarine tree—with color definitions (except those in common color terms) referenced to Maerz and Paul Dictionary of Color—are as follows:

Tree:
- *Size.*—Large for dwarf type. Average height — 6 feet.
- *Vigor.*—Medium.
- *Growth.*—Spreading.
- *Density.*—Open.
- *Form.*—Vase-formed.
- *Hardiness.*—Hardy.
- *Production.*—Productive.
- *Bearing.*—Regular bearer.

Trunk:
- *Size.*—Medium.
- *Texture.*—Medium.

Branches:
- *Size.*—Stocky.
- *Texture.*—Medium.
- *Lenticels.*—Number; medium.

Leaves:
- *Size.*—Large. Average length — $6\frac{1}{2}''$. Average width $1\frac{1}{4}''$.
- *Form.*—Lanceolate; acutely pointed.
- *Thickness.*—Medium.
- *Texture.*—Smooth.
- *Color.*—Top side — Medium green (23-L-8). Under side — Lighter green (22-I-6).
- *Margin.*—Crenate.
- *Petiole.*—Medium length — average $\frac{5}{8}''$.
- *Glands.*—Average number — 2 or 3; alternate; medium size; reniform; position — usually 2 or 3 on petiole and 1 or more on base of blade.

Flower buds:

*Hardiness.*—Hardy.

*Size.*—Medium.

*Length.*—Medium.

Flowers:

*Blooming period.*—Medium, as compared to other varieties.

*Size.*—Large.

*Color.*—Pink.

Fruit:

*Maturity when described.*—Eating ripe — July 9, 1980.

*Date of first picking.*—July 1, 1980.

*Date of last picking.*—July 7, 1980.

*Size.*—Medium. Average diameter axially — $2\frac{1}{2}''$. Average transversely in suture plane — 2 5/16".

*Form.*—Uniform. Symmetrical. Globose — oblong.

*Suture.*—Distinct.

*Cavity.*—Rounded.

*Base.*—Rounded.

*Apex.*—Short.

Skin:

*Thickness.*—Medium.

*Texture.*—Medium.

*Tendency to crack.*—None to slight.

*Down.*—Wanting.

*Color.*—Yellow (10-L-5) substantially overspread with red (5-L-4) shading to darker red (7-L-6).

Flesh:

*Color.*—Yellow (9-L-5). Surface of pit cavity: yellow shaded with red.

*Texture.*—Medium firm. Fine. Crisp.

*Fibers.*—Few.

*Ripens.*—Evenly.

*Flavor.*—Subacid.

*Aroma.*—Distinct.

*Eating quality.*—Good.

Stone:

*Type.*—Free.

*Size.*—Medium. Average length — $1\frac{1}{8}''$. Average breadth — 1". Average thickness — $\frac{7}{8}''$.

*Form.*—Globose — oblong.

*Base.*—Oblique.

*Apex.*—Rounded.

*Sides.*—Equal.

*Tendency to split.*—Slight.

*Color.*—Brown (7-C-12).

Use: Market; local; dessert.

Keeping quality: Medium.

Resistance to insects and diseases: No unusual susceptibilities noted.

Shipping quality: Medium.

The dwarf nectarine tree and its fruit herein described may vary in slight detail due to climatic and soil conditions under which the variety may be grown; the present description being of the variety as grown in the Central Valley of California.

I claim:

1. A new and distinct variety of dwarf nectarine tree substantially as shown and described.

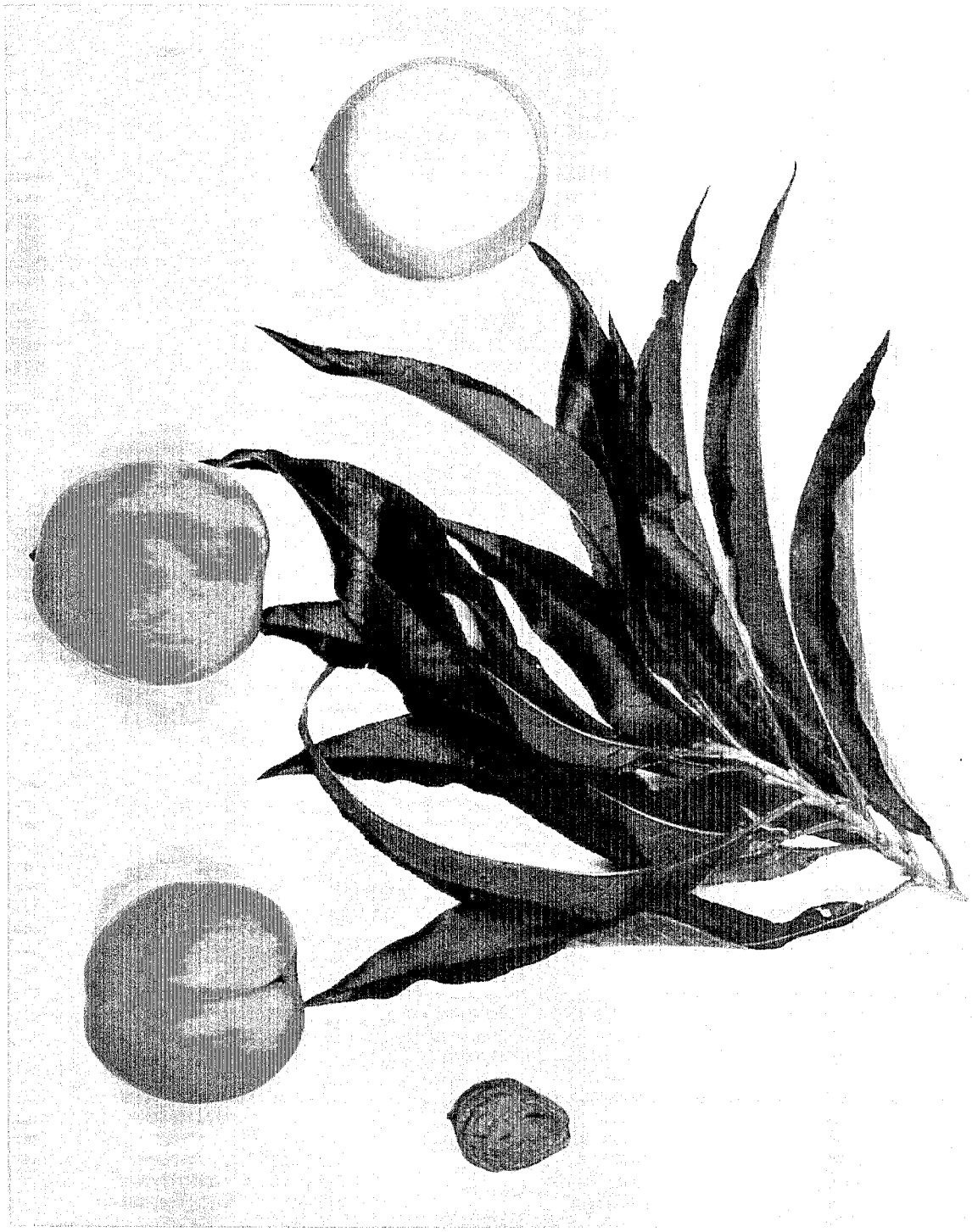

* * * * *